(12) United States Patent
Pethe

(10) Patent No.: US 10,989,362 B2
(45) Date of Patent: Apr. 27, 2021

(54) FLUID PROCESSING CONTROL SYSTEM AND RELATED METHODS

(71) Applicant: PALL TECHNOLOGY UK LIMITED, Portsmouth (GB)

(72) Inventor: Vishwas Pethe, Shakopee, MN (US)

(73) Assignee: PALL TECHNOLOGY UK LIMITED, Portsmouth (GB)

( * ) Notice: Subject to any disclaimer, the term of this patent is extended or adjusted under 35 U.S.C. 154(b) by 80 days.

(21) Appl. No.: 14/350,228

(22) PCT Filed: Oct. 5, 2012

(86) PCT No.: PCT/US2012/059013
§ 371 (c)(1),
(2) Date: Apr. 7, 2014

(87) PCT Pub. No.: WO2013/052836
PCT Pub. Date: Apr. 11, 2013

(65) Prior Publication Data
US 2014/0230929 A1    Aug. 21, 2014

Related U.S. Application Data

(60) Provisional application No. 61/544,416, filed on Oct. 7, 2011.

(51) Int. Cl.
*C12M 1/00* (2006.01)
*F17D 3/01* (2006.01)
*C12M 1/34* (2006.01)

(52) U.S. Cl.
CPC .............. *F17D 3/01* (2013.01); *C12M 21/00* (2013.01); *C12M 23/14* (2013.01); *C12M 23/58* (2013.01); *C12M 41/00* (2013.01); *Y10T 137/8158* (2015.04)

(58) Field of Classification Search
CPC ...... C12M 23/14; C12M 41/00; C12M 23/58; F17D 3/01; Y10T 137/8158
USPC ..................................... 435/289.1; 137/551
See application file for complete search history.

(56) References Cited

U.S. PATENT DOCUMENTS

| | | | | |
|---|---|---|---|---|
| 3,911,140 A | * | 10/1975 | Osborne ................ | C12M 47/10 426/36 |
| 5,081,035 A | * | 1/1992 | Halberstadt ............ | C12M 23/24 210/321.79 |
| 5,316,905 A | * | 5/1994 | Mori ...................... | C12M 41/40 435/286.1 |
| 5,443,985 A | | 8/1995 | Lu et al. | |

(Continued)

FOREIGN PATENT DOCUMENTS

| | | |
|---|---|---|
| CN | 102112594 A | 6/2011 |
| JP | H01206988 A | 8/1989 |

(Continued)

*Primary Examiner* — Liban M Hassan
(74) *Attorney, Agent, or Firm* — King & Schickli, PLLC

(57) ABSTRACT

In one aspect, a system for use in processing a fluid comprises a reservoir for holding the fluid and one or more bioreactors for receiving the fluid from the reservoir. One or more sensors are provided for sensing one or more parameters of the fluid, and corresponding control measures may be initiated. Regulators may also be provided for regulating various parameters of the fluid processing operation. Related systems and methods are also disclosed.

13 Claims, 5 Drawing Sheets

(56) References Cited

U.S. PATENT DOCUMENTS

| | | | |
|---|---|---|---|
| 5,510,262 A * | 4/1996 | Stephanopoulos | C12M 23/24 435/297.2 |
| 5,612,188 A * | 3/1997 | Shuler | C12M 23/58 435/286.5 |
| 6,455,306 B1 * | 9/2002 | Goldstein et al. | 435/372 |
| 6,673,008 B1 * | 1/2004 | Thompson | A01K 45/007 435/290.4 |
| 6,875,605 B1 * | 4/2005 | Ma | C12N 5/0647 435/297.1 |
| 7,682,823 B1 | 3/2010 | Runyon | |
| 2003/0054544 A1 * | 3/2003 | Gruenberg | 435/289.1 |
| 2003/0143727 A1 * | 7/2003 | Chang | 435/289.1 |
| 2005/0089993 A1 | 4/2005 | Boccazzi et al. | |
| 2005/0176143 A1 * | 8/2005 | Merchav | C12M 25/14 435/372 |
| 2005/0272146 A1 | 12/2005 | Hodge et al. | |
| 2007/0172945 A1 | 7/2007 | O'Kennedy et al. | |
| 2009/0137026 A1 * | 5/2009 | Kobayashi | C12M 23/12 435/286.4 |
| 2009/0215022 A1 | 8/2009 | Page et al. | |
| 2010/0120129 A1 | 5/2010 | Amshey et al. | |
| 2010/0242354 A1 | 9/2010 | Perkins et al. | |
| 2011/0003323 A1 | 1/2011 | Bargh | |
| 2011/0229397 A1 | 9/2011 | Bartel et al. | |

FOREIGN PATENT DOCUMENTS

| | | | |
|---|---|---|---|
| JP | H05123156 A | 5/1993 | |
| JP | 2009278991 A | 12/2009 | |
| WO | 2010048417 A2 | 4/2010 | |
| WO | 2010115185 A1 | 10/2010 | |
| WO | 2010121601 A2 | 10/2010 | |
| WO | WO 2010115185 A1 * | 10/2010 | C12M 21/08 |
| WO | 2011062621 A2 | 5/2011 | |

* cited by examiner

FLUID PROCESSING CONTROL SYSTEM AND RELATED METHODS

U.S. patent application Ser. No. 61/544,416 is incorporated herein by reference.

TECHNICAL FIELD

The present invention relates generally to the fluid processing arts and, more particularly, to a control system for controlling bioprocessing.

BACKGROUND OF THE INVENTION

Cells typically require homogenous growth media with optimum levels of oxygen, pH, nutrients (sugar, micronutrients, etc.), and temperature. This may be accomplished in a container, termed a bioreactor, for housing the cultured cells and media, usually under sterile conditions. Growing multiple batches of different cells or the same cells under different conditions thus requires the use of individually regulated bioreactors. Avoiding this individualized approach by providing a reservoir for supplying fluid to multiple bioreactors, while also permitting individualized control of one or more parameters and assurances as to validation of the individual bioreactors, is highly desirable from an efficiency and cost standpoint.

SUMMARY OF THE INVENTION

A system for use in processing a fluid including a reservoir for holding the fluid and one or more bioreactors for receiving the fluid from the reservoir. At least one first sensor is provided for sensing a first parameter of the fluid external to at least one bioreactor, and at least one second sensor is provided for sensing a second parameter of the fluid in the bioreactor(s).

In one embodiment, the system further includes a controller for controlling the first parameter of the fluid based at least partially on the second parameter of the fluid. The controller may be adapted to control a third parameter of the fluid in the reservoir. One or more of the first, second, and third parameter may be the same parameter, or may be different parameters.

The system may further include an intermediate vessel for receiving fluid from the reservoir and for delivering fluid to at least one bioreactor. The intermediate vessel may be adapted to deliver fluid to the plurality of bioreactors or to a single bioreactor. The controller may be adapted to control a third parameter of the fluid in the intermediate vessel.

The system may further include a receiver for receiving a signal from at least one first sensor and at least one second sensor. The receiver may be adapted to compare the parameter of the fluid before entering the bioreactor to the parameter of the fluid in at least one bioreactor.

The at least one first sensor may be associated with the reservoir and adapted to sense the first parameter of the fluid within the reservoir. The reservoir may also include a mixer, and the system may comprise a pump. At least one of the reservoir and the bioreactors may comprise a flexible bag. At least one of the bioreactors may comprise a roller bottle.

The reservoir may further include at least one port for receiving fluid from an effluent line of at least one bioreactor. The bioreactor(s) may further comprise a substrate for aiding in cellular growth. The substrate may comprise a material compatible with cell growth, including a fixed packing.

A bioreactor system for use in connection with a reservoir for holding a fluid comprises at least one bioreactor for receiving fluid from the reservoir. A first sensor senses a first parameter of the fluid external to the bioreactor, and a second sensor is for sensing a second parameter of the fluid in the bioreactor. A controller is provided for controlling at least the first parameter of the fluid based on the output of the sensor(s).

The system may include a receiver for receiving an output signal from the first and second sensors and for comparing the first and second parameters. The bioreactor may further include a substrate for aiding in cellular growth, such as a material compatible with cell growth. In one example, the substrate may comprise a tissue scaffold.

The at least one bioreactor may include an influent line for receiving fluid from the reservoir and an effluent line for delivering fluid from the bioreactor. The effluent line may recycle fluid to the reservoir.

The system may include a plurality of first sensors for measuring a plurality of first parameters of the fluid external to the bioreactor, and a plurality of second sensors for measuring a plurality of second parameters in the bioreactor. The reservoir may comprise a flexible bag, and the at least one bioreactor may also comprise a flexible bag. The system may include a plurality of bioreactors and a plurality of second sensors, each associated with at least one of the plurality of bioreactors.

A system may be provided for use in connection with a bioreactor including a sensor for sensing a parameter of a fluid within the bioreactor, said system comprising a reservoir for holding and delivering the fluid to the bioreactor, and at least one regulator for controlling a first parameter of the fluid external to the bioreactor based at least partially on a second parameter of the fluid within the bioreactor.

The system may include a plurality of regulators. Each regulator may be adapted to independently control a different parameter of the fluid. The regulator(s) may be adapted to control the parameter of the fluid within the reservoir. The regulator may also be adapted to control the parameter of the fluid between the reservoir and at least one bioreactor.

A method is also provided for validating a fluid parameter in a system including a reservoir and at least one bioreactor in fluid communication with the reservoir. The method may comprise sensing a common parameter in the reservoir and the bioreactor. The method may further include the step of comparing a first parameter sensed in the reservoir to a second parameter sensed in the bioreactor. The sensing in the bioreactor and the reservoir may be performed simultaneously or sequentially.

A method may also be provided for individually controlling a fluid parameter in at least one bioreactor used in association with a system including a reservoir. The method comprises adjusting a parameter of the fluid external to the reservoir and bioreactor. The method may further include the step of discarding the fluid from the bioreactor, and providing a plurality of bioreactors connected to the reservoir.

A method of bioprocessing comprises providing a reservoir in fluid communication with at least one bioreactor and providing a first sensor for sensing a first parameter of the fluid in the reservoir and a second sensor for sensing the first parameter of the fluid external to the reservoir. The method may include the step of regulating the fluid based on the first or second parameter. The method may further include the step of regulating the fluid based on the first and second parameter, as well as providing the second sensor in connection with the bioreactor.

A method of bioprocessing comprises controlling a parameter of a fluid in a reservoir; delivering the fluid to a bioreactor; and sensing the parameter in the bioreactor. The method may further include the step of adjusting the parameter of fluid before the fluid enters the bioreactor, based at least partially on the sensed parameter in the bioreactor. The delivering step may comprise delivering the fluid to a plurality of bioreactors, and the sensing step includes sensing the parameter in the plurality of bioreactors. The method may include the step of adjusting the parameter of the fluid entering a first bioreactor independent of the parameter of the fluid entering a second bioreactor.

In any disclosed embodiment, the parameter sensed may be selected from the group consisting of oxygen concentration, pH, nutrient level, temperature, $CO_2$, ammonia, cell biomass, or any combinations thereof.

BRIEF DESCRIPTION OF THE DRAWINGS

The accompanying drawings incorporated in and forming a part of the specification illustrate several aspects described herein and, together with the description, serve to explain the principles of the invention. In the drawings.

DETAILED DESCRIPTION OF THE INVENTION

Figure 1:
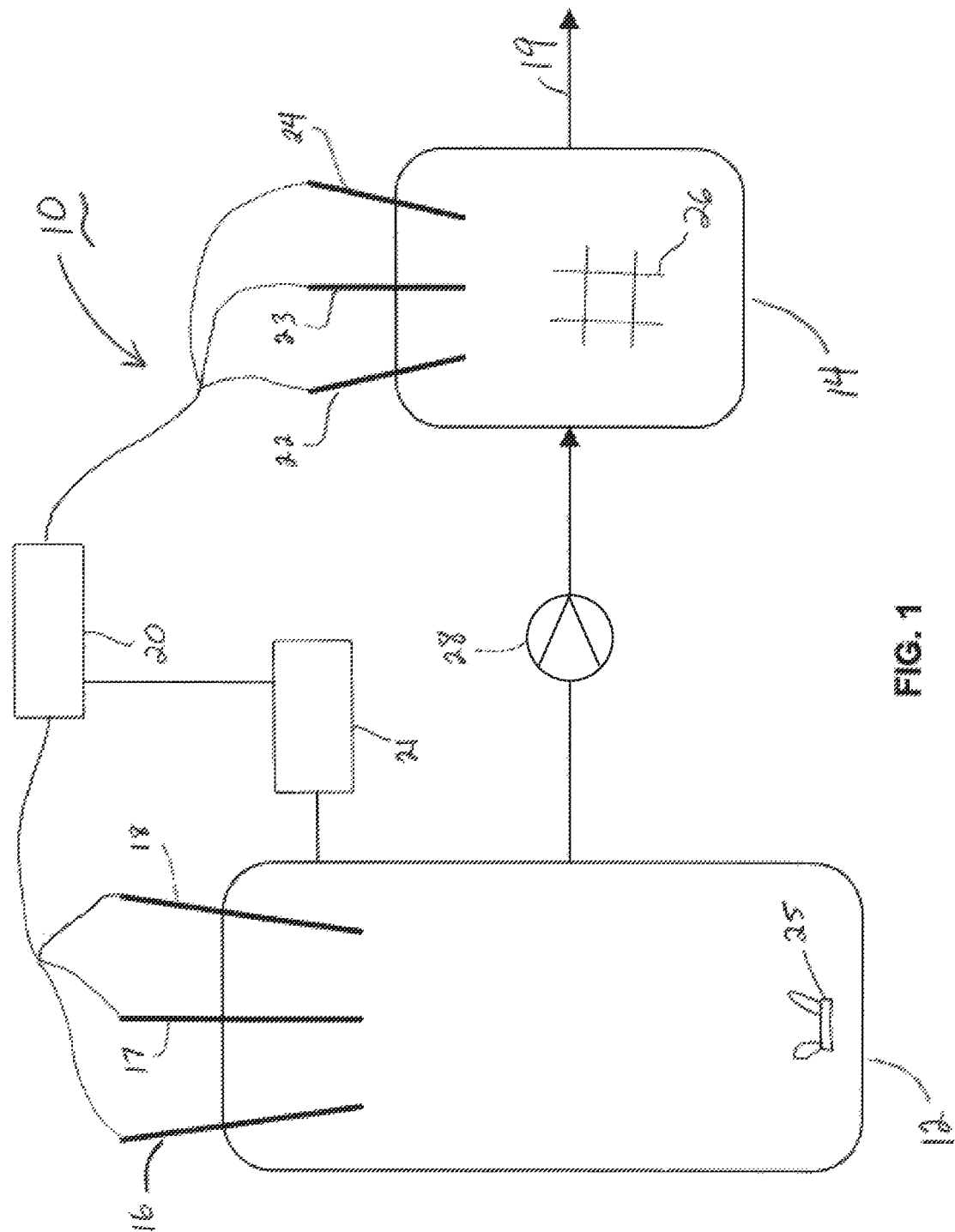
FIG. 1 is a schematic of a bioreactor system according to a first embodiment including a fluid parameter verification system.

Reference is now made to FIG. 1, illustrating a bioprocessing system including a fluid reservoir 12 connected to one or more process vessels. In one embodiment, the process vessels comprise bioreactors 14 adapted for receiving media and culturing cells. However, other vessels or containers for processing fluids could be used, alone or in combination with bioreactors 14.

The reservoir 12 may comprise a single-use, disposable container, such as a flexible vessel (such as a bag, which may be partially rigid), but may alternatively comprise a fully rigid container that can be disposed of or reused. Reservoir 12 may further include one or more ports (not pictured) for receiving a material for being introduced into the reservoir. The reservoir 12 may further include one or more filters associated with at least one of the ports to maintain sterile conditions within the reservoir. In one embodiment, the reservoir 12 is designed to prevent cellular growth within the reservoir. To this end, the reservoir 12 may be sterilized and may receive sterilized fluid.

The one or more bioreactors 14 may also comprise disposable, single-use vessels. For example, the bioreactors 14 may take the form of flexible vessels commonly called "bags," which may be completely flexible or partially flexible (e.g., having a rigid bottom). However, the bioreactors 14 could also comprise fully rigid containers as well, including for example a roller bottle.

To provide for the possible validation of the system 10 and, in particular, the individual bioreactors 14, a sensing arrangement may be provided. In one embodiment, this sensing arrangement is achieved by providing reservoir 12 with at least one first sensor 16 for sensing a parameter of the fluid therein, and a second sensor 22 for sensing either the same parameter in the bioreactor 14 or a different parameter, depending on the desired manner of bioprocessing being performed. This parameter may include a property of the fluid such as the oxygen concentration (i.e., dissolved oxygen), pH, nutrient level, temperature, $CO_2$, ammonia, cell biomass, a property of the system such as mixer speed, sparger air flow rate, or fluid flow rate, or combinations thereof.

The reservoir 12 may include one or more first sensors, such as sensors 16, 17, 18, for measuring the parameter(s), and the bioreactor 14 may include one or more second sensors, such as sensors 22, 23, 24, each for measuring the parameter(s) (which may be, for example, a comparative value of each of the parameters measured by the corresponding first sensors 16, 17, 18 in the reservoir 12). The first and second sensors may be attached to the walls of the reservoir 12 or bioreactor 14, and may perform sensing in a manner that does not interfere with the sterility of the fluid (e.g., optical or acoustic sensors). The sensors used may also be made to be disposable or single-use devices that may be discarded after use, or may be re-usable.

The system 10 may also optionally include a receiver 20 for receiving a signal from the first sensor 16 and from the second sensor 22 corresponding to a value of a measured parameter in the reservoir 12 and the bioreactor 14 (which, again, may be the same or different parameters). The receiver 20 may provide the respective values for comparison by an observer, or be associated with a processor to compare the value of the parameter in the reservoir 12 to the value of the parameter in the bioreactor 14, including when the parameters are the same (e.g., temperature). This comparison may be made in order to verify that the values correspond in both the reservoir and the bioreactor, thus providing a measure of validation. The determination may be whether the values are the same or, alternatively, may be made to verify that a difference between the two values is within an acceptable range (e.g., dissolved oxygen in the reservoir 12 is comparable to that in the bioreactor 14).

In accordance with one embodiment, the system 10 may further include means for directing fluid from the reservoir 12 to the bioreactor 14, such as a pump 28. The pump 28 may continuously or selectively deliver fluid from the reservoir 12 to the bioreactor 14. Alternatively, the system 10 may be assembled to deliver fluid from the reservoir to the bioreactor by other means, such as gravity flow. Suitable valve and tubing arrangements may also be used to control the flow in the desired manner.

The receiver 20 may signal a user of the results of the comparison, or may implement a measure of automated control over the parameter (e.g., heating or cooling in the case where temperature is the parameter) to achieve a pre-determined or desired outcome. For example, a controller 21 may be provided for controlling at least one parameter of the fluid in the reservoir 12. As an example, the reservoir 12 may include an aeration device, such as a sparger, for delivering oxygen to the fluid therein, and the controller 21 may control the airflow provided to the sparger. Other components associated with the controller 21 may include any number of devices for delivering additives to the reservoir (such as nutrients or pH adjusting agents), a temperature control device, or any other element for controlling a desired parameter.

The reservoir 12 may further include a mixer 25 for agitating the contents. The mixer 25 may comprise an impeller or any other suitable device for agitating fluid in the reservoir. For example, the mixer 25 comprises a disposable magnetic impeller including one or more blades, or another type of mixer that allows for sterile conditions to be maintained (e.g., a sleeve containing a paddle or rod and adapted for rotating within the compartment of the reservoir 12 for containing the fluid). Responsive to input from any sensor or the operator, the controller 21 may also exercise control over the speed of rotation of the mixer 25, such as by being associated with a corresponding motive device (which may comprise a motor).

Bioreactor 14 may also include an effluent line 19. In one embodiment, this effluent line 19 discharges fluid from the system 10. In another embodiment, the effluent line 19 recycles fluid from the bioreactor 14 back to the reservoir 12.

The bioreactor 14 may also include a mixer. For example, the mixer may comprise an impeller or the like that allows for sterile conditions to be maintained. The bioreactor 14 may also comprise a sparger (also not shown). The bioreactor 14 may be, for example, of the type described in U.S. Pat. No. 7,384,027, the disclosure of which is incorporated herein by reference.

In one embodiment, bioreactor 14 may further include a substrate 26 for aiding in cellular growth. The substrate 26 may comprise any suitable carrier such as mineral carriers (e.g. silicates or calcium phosphate), organic compounds such as porous carbon, natural products such as chitosan, polymers or biopolymers compatible with cell growth. The substrate 26 can have the form of beads with regular or irregular structure, or any other material compatible with cell growth. The substrate 26 can also be provided as a single piece with pores and or channels. In one embodiment, a bioreactor 14 may comprise a roller bottle. In another embodiment, the bioreactor 14 may be provided as described in U.S. Pat. Nos. 8,137,959 or 7,384,027, the disclosures of which are incorporated by reference.

Figure 2:
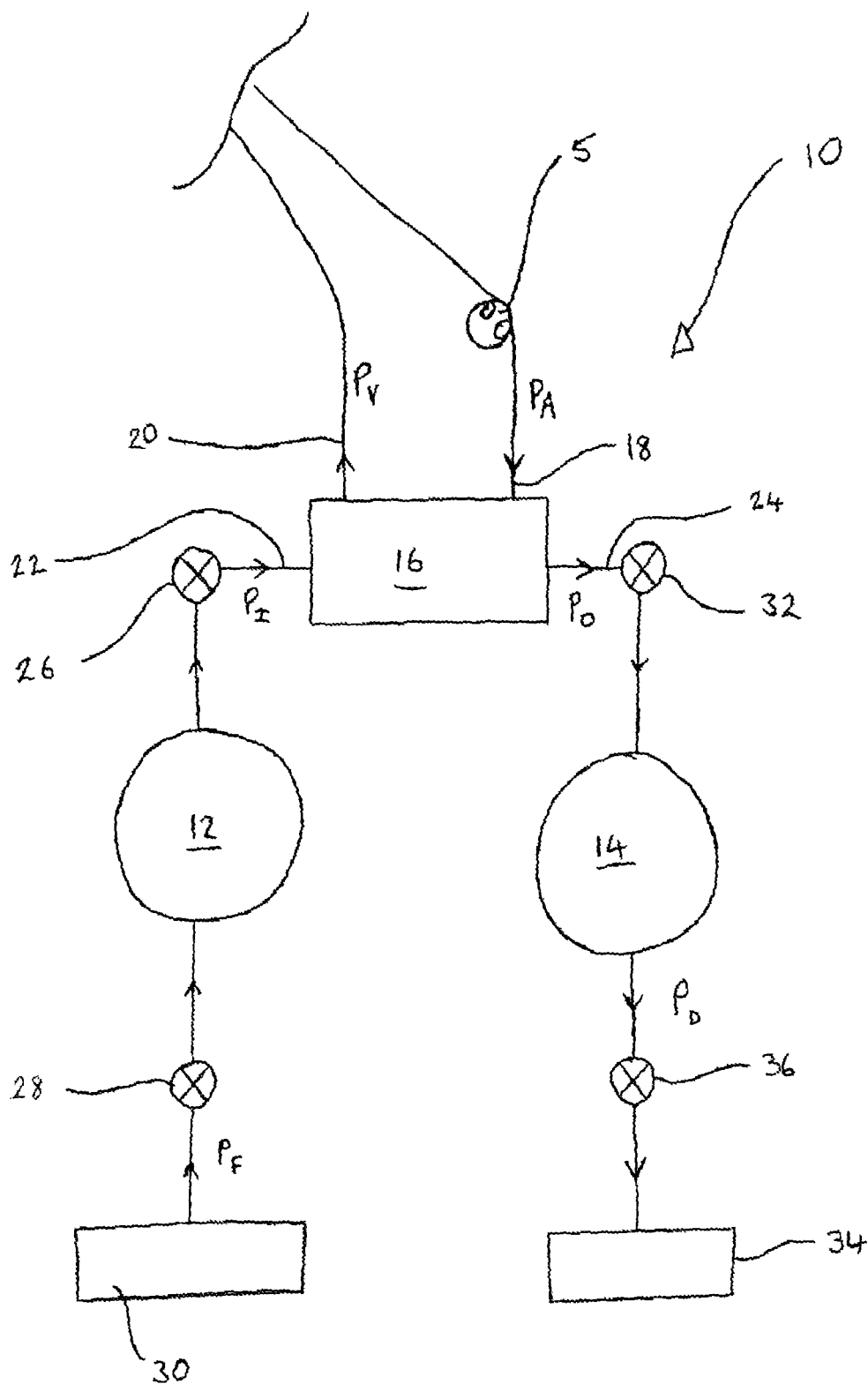
FIG. 2 is a schematic of the system of FIG. 1 including multiple bioreactors.

With reference to FIG. 2, a further embodiment of a system 30 is illustrated comprising a reservoir 12 for holding a fluid and a plurality of bioreactors 14a . . . 14n for receiving the fluid from a common reservoir 12. This system 30 includes the validation arrangement described above as applied to multiple bioreactors, such as for example four bioreactors 14a, 14b, 14c, 14d, each of which is associated with a sensor 22a-22d for sensing a desired parameter of the fluid. The reservoir 12 includes a corresponding sensor 16 for sensing the same parameter of the fluid, and pumps 28 may be provided for facilitating fluid transfer to the bioreactors 14a-14d. The fluid from the bioreactors may be discarded or re-circulated back to the reservoir 12.

Figure 3:
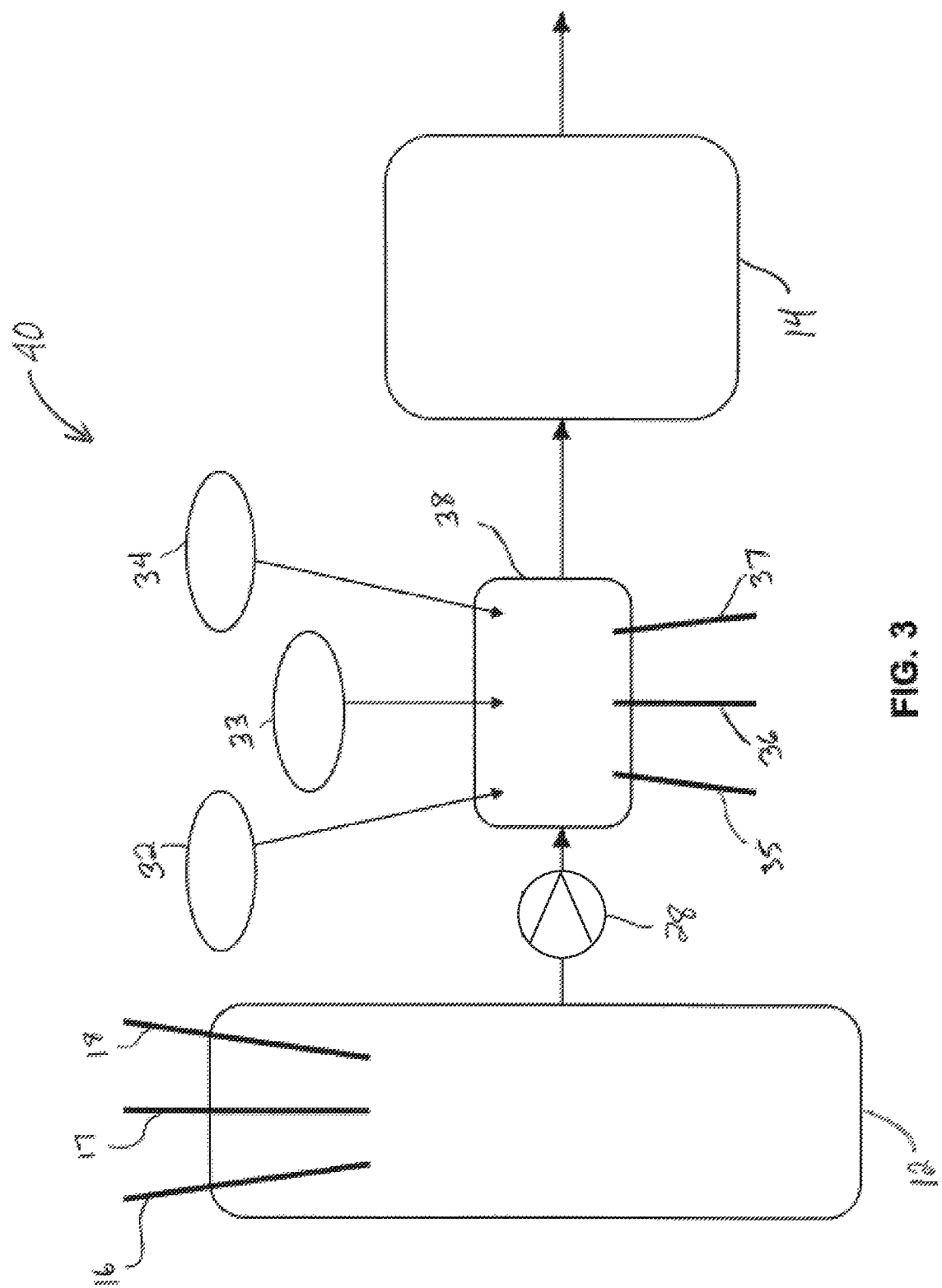
FIG. 3 is a schematic of a system providing for individualized bioreactor control.

Turning to FIG. 3, a system 40 in another embodiment allows for adjustment of the fluid parameter once the fluid exits the reservoir 12 but before reaching an external vessel, such as the bioreactor 14. In one embodiment, this is achieved by providing a regulator 32 for regulating the fluid parameter in a line for delivering fluid from the reservoir 12 to the bioreactor 14. The regulator 32 may comprise any instrument capable of adjusting a fluid parameter, such as an oxygen source, a pH source, a nutrient source, or a thermal regulator (e.g., heater or chiller) to alter temperature. The system 40 may include a plurality of regulators 32, 33, 34 for controlling a plurality of parameters of the fluid before entering the bioreactor 14. The fluid may be discarded from the bioreactor 14, but could possibly be re-circulated as well.

The system 40 may further include at least one intermediate sensor 35 for sensing a value of the parameter of the fluid before entering the bioreactor 14. This sensor 35 may be in communication with the regulator 32 for determining whether or not the parameter should be adjusted, and/or the degree to which the adjustment should be made. This intermediate sensor 35 may be used much like the validation system 10 previously described. Specifically, the first sensor 16 of the reservoir 12 and the intermediate sensor 35 may be in communication with a processor for comparing one or more values of the parameter(s) at each location. If the difference in values is not within a predetermined range, the regulator 32 may adjust the value of the parameter(s) of the fluid before entering the bioreactor 14. A plurality of intermediate sensors 35, 36, 37 may also be provided for measuring the plurality of fluid parameters measured by the plurality of first sensors 16, 17, 18 and adjusted by the plurality of regulators 32, 33, 34.

In accordance with one embodiment, the regulator 32 may be associated with an intermediate vessel 38 capable of receiving fluid from the reservoir 12 and delivering fluid to the bioreactor 14. The intermediate vessel 38 may further include a mixer to agitate the fluid before entering the bioreactor 14. The intermediate vessel 38 may comprise a fully rigid container, a flexible bag, or any other container for temporarily holding fluid between the reservoir 12 and the bioreactor 14.

The system 40 may include at least one means for delivering fluid from the reservoir 12 to the bioreactor 14, such as pump 28. In one embodiment, an additional delivery means may be provided for removing fluid from the bioreactor. In the case of an intermediate vessel 38, the system may include a first pump 28 for delivering fluid from the reservoir 12 to the intermediate vessel 38 and a second pump (not shown) for delivering the fluid downstream to bioreactor 14.

Figure 4A:
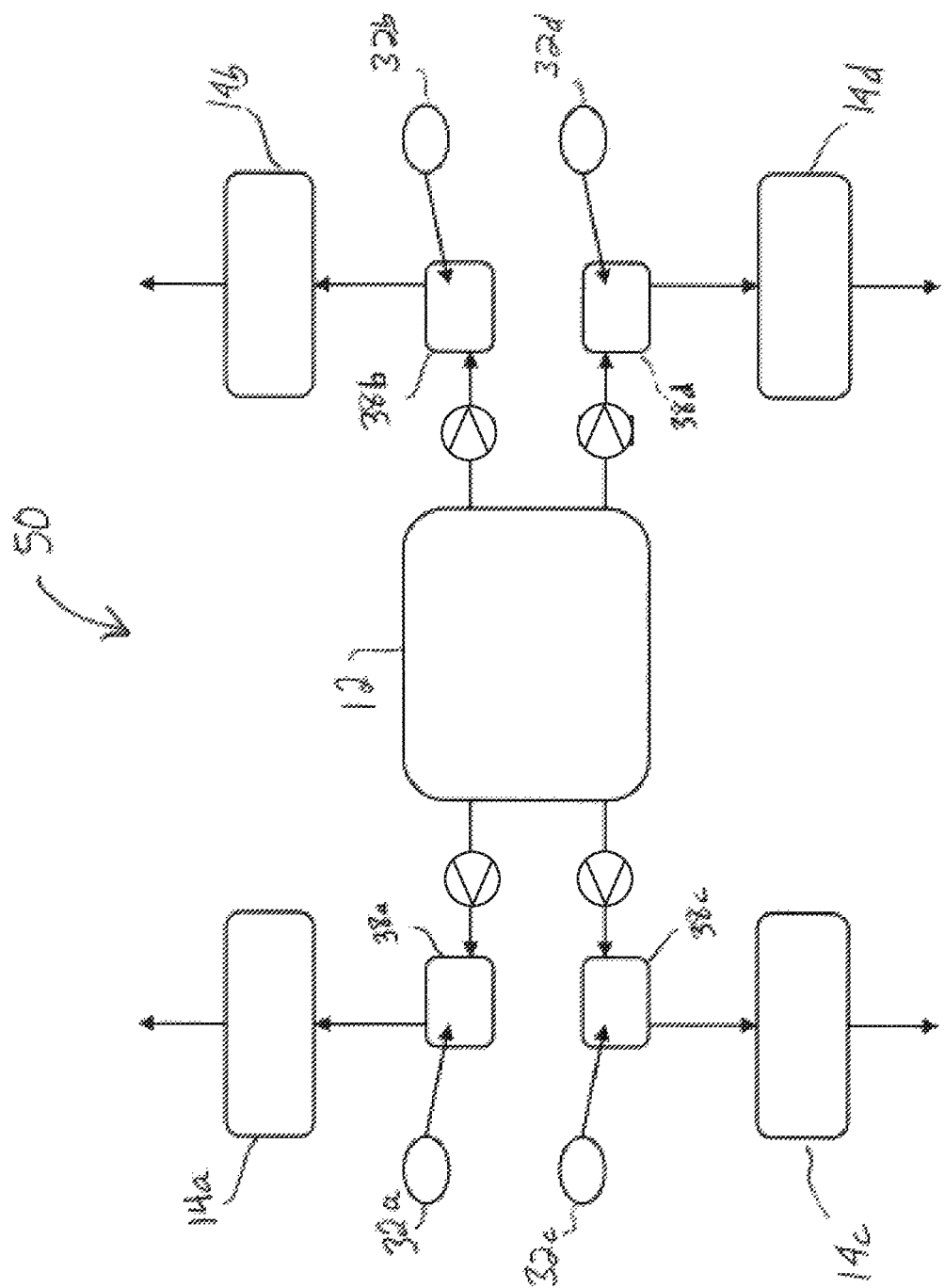
FIG. 4a is a schematic of a first embodiment of the system of FIG. 3 including multiple bioreactors.

FIG. 4a illustrates another embodiment of a system 50 including the adjustment capacity illustrated in FIG. 3. In system 50, the reservoir 12 supplies fluid to a plurality of bioreactors, which is shown as four bioreactors 14a-14d for purposes of illustration but could be any number. A plurality of regulators 32a, 32b, 32c, 32d are provided for regulating the parameter of the fluid before entering the respective bioreactors 14a-14d, along with intermediate vessels 38a, 38b, 38c, and 38d. Each regulator 32a-32d controls the parameter of the fluid delivered to a single bioreactor 14a-14d, which allows a user to operate multiple bioreactors utilizing a common homogeneous fluid, while permitting at least one specific parameter to be varied among each bioreactor. This may be particularly important in a research setting in which various parameters may be manipulated within strict controls to optimize cellular growth conditions.

Figure 4B:
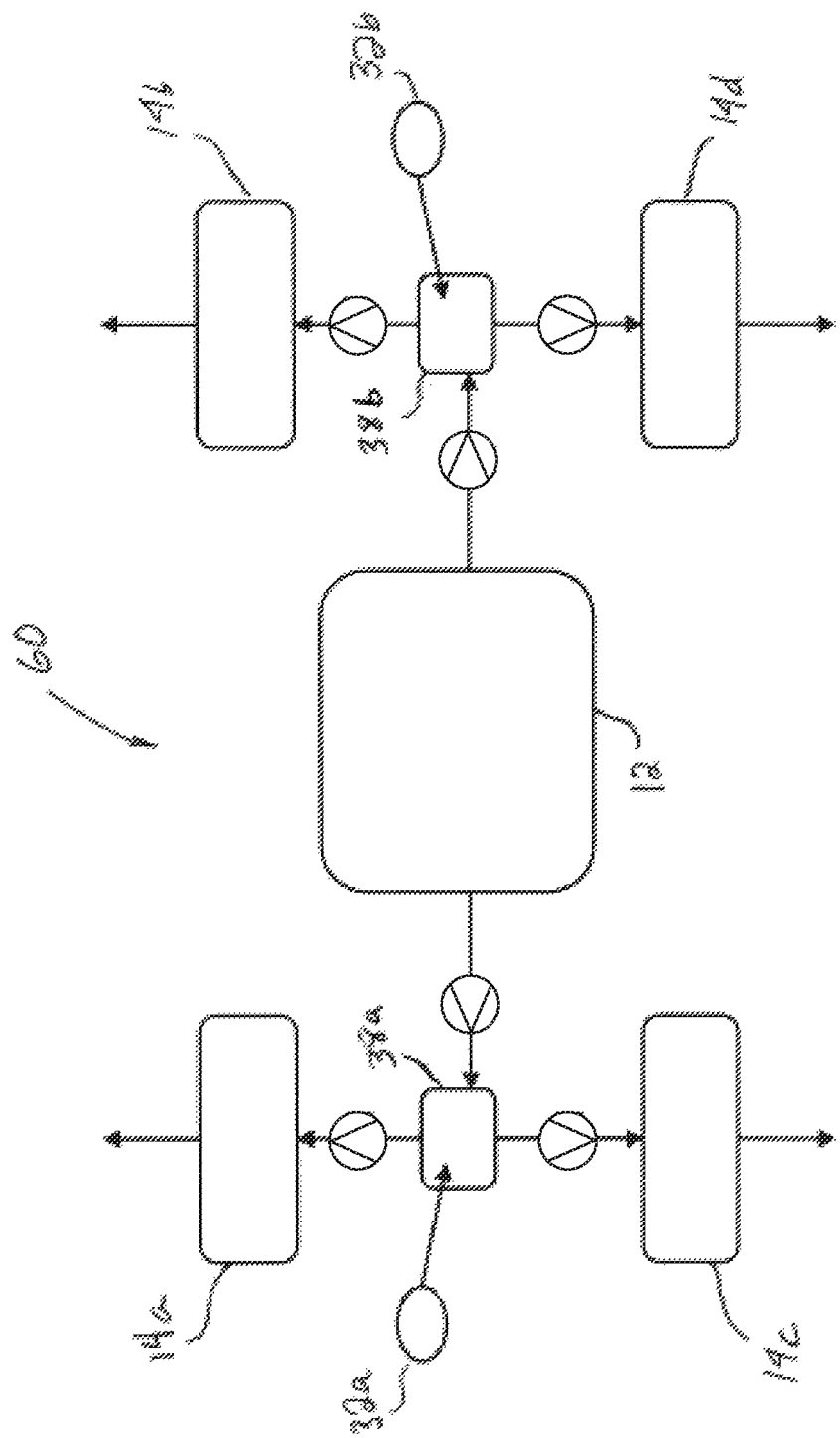
FIG. 4b is a schematic of a second embodiment of the system of FIG. 3.

FIG. 4b illustrates an alternate embodiment of a system 60 in which each of a plurality of bioreactor 14a . . . 14n may receive fluid having a parameter controlled by a single regulator. For example, as illustrated in FIG. 4b, regulator 32a controls the fluid delivered to bioreactors 14a and 14c, while regulator 32b controls the fluid delivered to bioreactors 14b and 14d. Each of the regulators 32a, 32b may be associated with a respective intermediate vessel 38a, 38b, which may include a mixer for ensuring a homogenized fluid before delivery to the corresponding bioreactor 14a . . . 14n.

This embodiment offers similar advantages in the field of research as the embodiment of FIG. 4a, but also offers certain advantages in commercial production applications. For example, multiple products produced in similar, but distinct cellular growth environments may utilize a common reservoir 12 as a source of fluid, with each of regulators 32a, 32b independently adjusting the conditions for the cells grown in multiple different sets of reactors. Similarly, a common fluid may be created in reservoir 12 that may be used to grow multiple different cell types. The system 60 then allows for each regulator to independently control the media optimized for a particular cell type in each reactor set.

The foregoing descriptions of several embodiments are presented for purposes of illustration and description. The embodiments described are not intended to be exhaustive or to limit the invention to the precise form disclosed. Modifications or variations are possible in light of the above teachings. For example, while several fluid parameters are mentioned as being adjusted in response to sensing, it should be understood that the parameter adjustment may comprise altering a physical characteristic of the system, such as the movement of a mixer, the volume of gas delivery, or any other physical parameter of the system that may alter the bioprocessing operation. The embodiments described were chosen to provide the best illustration of the principles of the invention and its practical application to enable one of ordinary skill in the art to utilize the invention in various embodiments and with various modifications as are suited to the particular use contemplated. All such modifications and variations are within the scope of the invention interpreted in accordance with the breadth to which it is fairly, legally, and equitably entitled.

The invention claimed is:

1. A system for use in processing a fluid, comprising:
   a reservoir for holding the fluid;
   a plurality of bioreactors in fluid communication with the reservoir and configured to receive the fluid from the reservoir;
   a plurality of intermediate vessels in fluid communication with the reservoir, each of said plurality of intermediate vessels being intermediate the reservoir and a respective at least one of the plurality of bioreactors, and each of said plurality of intermediate vessels configured to receive the fluid from the reservoir and to deliver the fluid to the respective at least one of the plurality of bioreactors, wherein a single one of the plurality of intermediate vessels is between the reservoir and any one of the plurality of bioreactors;
   a plurality of first pumps, each of said first pumps between each of the plurality of intermediate vessels and the respective at least one of the plurality of bioreactors, said first pumps adapted for delivering fluid from said each of the plurality of intermediate vessels to the respective at least one of the plurality of bioreactors;
   at least one first sensor for sensing a first parameter of the fluid in the reservoir;
   a plurality of second sensors, each of said second sensors being associated with a respective one of the plurality of intermediate vessels, each of said plurality of second sensors adapted for sensing a second parameter of the fluid in said respective one of the plurality of intermediate vessels;
   a processor communicating with the at least one first sensor and the plurality of second sensors, the processor configured to compare the first parameter of the fluid to the second parameter of the fluid in the plurality of intermediate vessels; and
   a plurality of regulators communicating with the processor, each of said regulators being associated with said respective one of the plurality of intermediate vessels and configured to independently control the second parameter of the fluid in said respective one of the plurality of intermediate vessels, based on a comparison of the first and second parameters by the processor.

2. The system of claim 1, further including a mixer for mixing the fluid in the reservoir.

3. The system of claim 1, further including a plurality of second pumps, each of said second pumps located between the reservoir and each of the plurality of intermediate vessels, said second pumps adapted for delivering fluid from the reservoir to each of the plurality of intermediate vessels.

4. The system of claim 1, wherein at least one of the plurality of bioreactors comprises a flexible bag.

5. The system of claim 1, wherein at least one of the plurality of bioreactors comprises a roller bottle.

6. The system of claim 1, further including an effluent line for recycling fluid from at least one of the plurality of bioreactors to the reservoir.

7. The system according to claim 1, wherein at least one of the plurality of bioreactors further comprises a substrate for aiding in cellular growth.

8. The system of claim 1, wherein each of said plurality of intermediate vessels is adapted to deliver fluid to at least two of the plurality of bioreactors without said fluid first flowing through another of said plurality of bioreactors.

9. A bioreactor system for use in connection with a fluid, comprising:
   a reservoir for retaining the fluid;
   a plurality of bioreactors comprising a plurality of sets of bioreactors, each of the sets of bioreactors in fluid communication with the reservoir and configured to receive the fluid from the reservoir without said fluid first passing through another of the plurality of bioreactors;
   a plurality of intermediate vessels, each of said plurality of intermediate vessels associated with only one of the plurality of sets of bioreactors, and each of said plurality of intermediate vessels in fluid communication with the reservoir and with said one of the plurality of sets of bioreactors and configured to receive the fluid from the reservoir and deliver said fluid to said one of the plurality of sets of bioreactors;
   at least one first sensor for sensing a first parameter of the fluid in the reservoir;
   a plurality of second sensors, each of said second sensors being associated with a respective one of the plurality of intermediate vessels, each of said plurality of second sensors adapted for sensing a second parameter of the fluid in said respective one of the plurality of intermediate vessels;
   at least one regulator associated with each of the plurality of intermediate vessels;
   a processor communicating with the at least one regulator, the processor configured to compare the first parameter of the fluid to the second parameter of the fluid in the plurality of intermediate vessels, each regulator configured to independently control the second parameter of the fluid within said each of said plurality of intermediate vessel with which said regulator is associated based upon a comparison of the first and second parameters by the processor; and
   a plurality of pumps, at least one of said plurality of pumps located between each of the plurality of intermediate vessels and at least one of the plurality of bioreactors.

10. A bioprocessing system for use in processing a fluid, said system comprising:
   a plurality of bioreactors;
   a reservoir adapted for holding the fluid for delivery to the plurality of bioreactors;

a plurality of intermediate vessels, each of said plurality of intermediate vessels including a sensor for sensing a parameter of the fluid within said each of said plurality of intermediate vessels, and each of the plurality of intermediate vessels being in fluid communication with the reservoir and a single one of the plurality of bioreactors, each of said plurality of intermediate vessels configured to receive fluid from the reservoir and to deliver fluid to the single one of the plurality of bioreactors;

at least one first sensor for sensing a first parameter of the fluid in the reservoir;

a plurality of second sensors, each of said second sensors being associated with a respective one of the plurality of intermediate vessels, each of said plurality of second sensors adapted for sensing a second parameter of the fluid in said respective one of the plurality of intermediate vessels;

a processor communicating with the at least one first sensor and the plurality of second sensors in each of said plurality of intermediate vessels, the processor configured to compare the first parameter of the fluid to the second parameter of the fluid in the plurality of intermediate vessels;

a first regulator associated with a first of the plurality of intermediate vessels, and a second regulator associated with a second of the plurality of intermediate vessels, said first regulator and said second regulator communicating with the processor, said first regulator configured to regulate a first parameter of the fluid in the first of the plurality of intermediate vessels and said second regulator configured to regulate the first parameter of the fluid in the second of the plurality of intermediate vessels independent of the first regulator, based on a comparison of the first parameter with the second parameter by the processor; and a plurality of pumps, each of said pumps located between each of the plurality of intermediate vessels and the single one of the plurality of bioreactors in fluid communication with said each of the plurality of intermediate vessels.

11. The bioreactor system of claim 9, further including a mixer in at least one of the plurality of intermediate vessels.

12. The system of claim 1, wherein the parameter is selected from the group consisting of oxygen concentration, pH, nutrient level, temperature, $CO_2$, ammonia, cell biomass, or any combination thereof.

13. The system of claim 1, wherein the plurality of bioreactors are provided in the form of multiple different sets of bioreactors.

\* \* \* \* \*